US006781032B1

(12) United States Patent
Gruissem et al.

(10) Patent No.: US 6,781,032 B1
(45) Date of Patent: Aug. 24, 2004

(54) HOMOLOGOUS RECOMBINATION IN PLANTS

(75) Inventors: Wilhelm Gruissem, Berkeley, CA (US); John Jelesko, San Jose, CA (US); Masaki Furuya, Tokyo (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/134,014

(22) Filed: Aug. 14, 1998

(51) Int. Cl.[7] .................. C12N 15/82; C12N 15/53; C12N 15/62; C12N 15/84
(52) U.S. Cl. .................. 800/278; 800/288; 800/294; 800/306; 435/8; 435/69.7; 435/430; 435/430.1; 435/463; 435/468; 435/469
(58) Field of Search .................. 435/8, 69.7, 430, 435/430.1, 463, 468, 469; 800/278, 288, 294, 306

(56) References Cited

U.S. PATENT DOCUMENTS 5,658,772 A * 8/1997 Odell et al. ............... 435/172.3

OTHER PUBLICATIONS

Bent, A.F. Plant Physiology 124: 1540–1547 (Dec. 2000).*
Miao et al. Plant J. 7(5):359–365, 1995.*
Risseeuw et al. Plant J. 11(4):717–728, 1997.*
Thykjaer et al. Plant Mol. Biol. 35(4):523–530, 1997.*
Staub et al. Plant J. 7(5):845–848, 1995.*
Ow et al. Science 234: 856–859, Nov. 1986.*
Swoboda et al. EMBO J. 13(2):484–489, 1994.*
Lyznik et al. Mol. Gen. Genet. 230(1–2):209–218, 1991.*
Assaad, et al., *Genetics,* "Somatic and Germinal Recombination of a Direct Repeat in Arabidopsis", 132:553–566 (1992).
Tovar, et al., *Plant Cell,* "Somatic and Meiotic Chromosomal Recombination between Inverted Duplications in Transgenic Tobacco Plants", 4:319–332 (1992).
Bauer, et al., *Mol. Cell. Biol.* "Intermolecular Homologous Recombination in Plants", 10:492–500 (1990).
Chiurazzi, et al., *Plant Cell,* "Enhancement of Somatic Intrachromosomal Homologous Recombination in Arabidopsis by the HO Endonuclease", 8(11):2057–2066 (1996).
Hrouda, et al., *Mol. Genet.* "High Fidelity Extrachromosomal Recombination and Gene Targeting in Plants", 243:106–111 (1994).
Lebel, et al., *Proc. Natl. Acad. Sci. USA,* "Stress–induced Intrachromosomal Recombination in Plant Somatic Cells", 90:422–426 (1993).
Offringa, et al., *Proc. Natl. Acad. Sci. USA,* "Nonreciprocal Homologous Recombination between Agrobacterium Transferred DNA and a Plant Chromosomal Locus", 90:7346–7350 (1993).

Offringa, et al., *EMBO J.* "Extrachromosomal Homologous Recombination and Gene Targeting in Plant Cells After Agrobacterium Mediated Transformation", 9:3077–3084 (1990).
Risseeuw, et al., *Plant J.* "Targeted Recombination in Plants Using Agrobacterium Coincides with Additional Rearrangements at the Target Locus", 7:109–119 (1995).
Puchta, et al., *Proc. Natl. Acad. Sci. USA,* "Two Different but Related Mechanisms are Used in Plants for the Repair of Genomic Double–strand Breaks by Homologous Recombination", 93:5055–5060 (1996).
Puchta, et al., *Nuc. Acids Res.,* "Homologous Recombination in Plant Cells is Enhanced by In Vivo Induction of Double Strand Breaks into DNA by a Site–specific Endonuclease" 21:5034–5040 (1993).
Puchta, et al., *Plant Mol. Biol.,* "Somatic Intrachromosomal Homologous Recombination Events in Populations of Plant Siblings", 28:281–292 (1995).
Puchta, et al., *Mol. Cell. Biol.,* "Extrachromosomal Homologous DNA Recombination in Plant Cells is Fast and is Not Affected by CpG Methylation", 12:3372–3379 (1992).
Puchta, et al., *Nuc. Acids Res.* A Transient Assay in Plant Cells Reveals a Positive Correlation Between Extrachromosomal Recombination Rates and Length of Homologous Overlap, 19:2693–2700 (1991).
Puchta, et al., *Mol. Gen. Genet.,* "The Mechanism of Extrachromosomal Homologous DNA Recombination in Plant Cells", 230:1–7 (1991).
Paszkowski, et al., *EMBO J.,* "Gene Targeting in Plants", 7:4021–4026 (1988).
Peterhans, et al., *EMBO J.,* "Intrachromosomal Recombination in Plants", 9:3437–3466 (1990).
Buerstedde, et al., *Cell,* "Increased Ratio of Targeted to Random Integration after Transfection of Chicken B Cell Lines", 67:179–88 (1991).
Jasin, et al., *Genes and Devel.,* "Homologous Integration in Mammalian Cells without Target Gene Selection", 2:1353–63 (1988).
Sedivy, et al., *Proc. Natl. Acad. Sci. USA,* "Positive Genetic Selection for Gene Disruption im Mammalian Cells by Homologous Recombination", 86:227–31 (1989).

* cited by examiner

Primary Examiner—David T. Fox
(74) Attorney, Agent, or Firm—Townsend and Townsend and Crew LLP (57) ABSTRACT

The present invention provides novel methods for modifying target nucleotide sequences in a plant cell through the use of homologous recombination. The plant cell is transformed with a DNA construct comprising a polynucleotide sequence encoding a fusion polypeptide comprising a polypeptide sequence of interest linked to a reporter sequence.

9 Claims, 2 Drawing Sheets

HOMOLOGOUS RECOMBINATION IN PLANTS

FIELD OF THE INVENTION

The present invention relates generally to methods for transforming plant cells and, more particularly, to methods for identifying plants in which a target DNA sequence has been modified by homologous recombination.

BACKGROUND OF THE INVENTION

Efficient methods for identifying plant cells in which homologous recombination has occurred is extremely useful in developing new plant varieties with targeted replacement or alteration of endogenous genes. Activation of a reporter gene activity due to homologous recombination between two non-allelic mutant copies of a reporter gene or between two overlapping deletions of a reporter gene have been reported in the literature (see, Assaad, et al., *Genetics*, 132:553–566 (1992); Tovar, et al., *Plant Cell*, 4:319–332 (1992); Baur, et al., *Mol. Cell. Biol.*, 10:492–500 (1990); Chiurazzi, et al., *Plant Cell*, 8(11):2057–2066 (1996); Hrouda, et al., Mol. Gen. Genet. 243:106–111 (1994); Lebel, et al., *Proc. Natl. Acad. Sci. USA*, 90:422–426 (1993); Lyznik, et al., *Mol. Gen. Genet.* 230:209–218 (1991); Offringa, et al. *Proc. Natl. Acad. Sci. USA*, 90:7346–7350 (1993); Offringa, et al., *EMBO J*, 9:3077–3084 (1990); Swoboda, et al., *EMBO J*, 13:484–489 (1994); Risseeuw, et al., *Plant J*, 7:109–119 (1995); Puchta, et al., *Proc. Natl. Acad. Sci. USA* 93:5055–5060 (1996); Puchta, et al., *Plant Mol. Biol.* 28:281–292 (1995); Puchta, et al., *Nuc. Acids Res.*, 21:5034–5040 (1993); Puchta, et al., *Mol. Cell. Biol.*, 12:3372–3379 (1992); Puchta, et al., *Nuc. Acids Res.* 19:2693–2700 (1991); Puchta, et al., *Mol. Gen. Genet.*, 230:1–7 (1991); Paszkowski, et al., *EMBO J*, 7:4021–4026 (1988); Peterhans, et al., *EMBO J.*, 9:3437–3446 (1990)). However, these reports are limited to identifying recombination events within genes which themselves had some inherent "reporter gene activity" (e.g. drug resistance or conversion of a calorimetric substrate). In most cases, the homologous recombination events were non-reciprocal (unidirectional) homology dependent events, referred to as gene conversion events.

Several reports in animal gene targeting experiments use a dominant selectable reporter gene as part of a Δgene X::reporter gene fusion to select for homologous recombination events in vivo (Buerstedde, et al., *Cell*, 67:179–88 (1991); Jasin, et al., *Genes and Devel.*, 2:1353–63 (1988); Sedivy, et al., *Proc. Natl. Acad. Sci. USA*, 86:227–31 (1989)). In all cases, the reporter genes used imparted resistance to a drug that was used as a dominant positive selection for those cells that underwent the specific homologous recombination between the Δgene X::reporter gene and the endogenous gene. A dominant selection approach can be problematic because either an insufficient level of the drug resistance trait or a tissue specific gene X expression pattern of the drug resistance trait may result in an inability to survive the drug selection during cell culture. The same concerns regarding the level and tissue specific expression pattern of the recombinant gene X'/X::reporter gene apply to the situations of using a dominant selectable reporter gene on a whole organism-based screen.

Although progress has been made, efficient screening methods for detecting homologous recombinants, particularly in plant cells is needed in the art. The present invention provides these and other advantages.

SUMMARY OF THE INVENTION

The present invention provides compositions and methods which use a reporter sequence to identify homologous recombinants in a large population of transformed plants or plant cells. The methods of the invention involve contacting plant cells with a nucleic acid molecule comprising a fusion polynucleotide sequence comprising a polypeptide sequence of interest linked to a reporter sequence, wherein the nucleic acid molecule lacks sequences necessary for expression of the fusion polynucleotide sequence gene product in a cell. The fusion polynucleotide sequence gene product is then detected in the plant cells, thereby identifying plant cells in which homologous recombination has occurred.

The means by which the fusion polynucleotide is introduced into the cell is not critical. Typically, the polynucleotide is introduced using a T-DNA vector. In some embodiments, plants are regenerated from the plant cells before the step of detecting the presence of the fusion sequence gene product.

The particular reporter sequence used in the methods is also not critical, for instance, non-selective markers such as luciferase can be used. In this case video imaging equipment is conveniently used to detect the luciferase.

The homologous recombination event can be used to alter endogenous gene in any number of ways. For instance, the recombination can result in gene conversion or may lead to inactivation of the endogenous gene. Alternatively, a recombinant allele derived from two related genes can be produced. The newly created recombinant allele will typically have a new activity as compared to either of the genes from which it was derived.

The invention also provides isolated nucleic acid molecule useful in the above methods, as well as plants produced by the methods.

Definitions

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non-equivalent cross-over events. Equivalent crossing over occurs between two equivalent sequences or chromosome regions, whereas nonequivalent crossing over occurs between identical (or substantially identical) segments of nonequivalent sequences or chromosome regions. Unequal crossing over typically results in gene duplications and deletions. For a description of the enzymes and mechanisms involved in homologous recombination see, Watson et al., *Molecular Biology of the Gene* pp 313–327, The Benjamin/Cummings Publishing Co. 4th ed. (1987).

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and their progeny. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as an $R_1$ generation transgenic plant. Transgenic plants which arise from sexual cross or by selfing are descendants of such a plant.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miner, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30 ° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising FIE nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

BRIEF DESCRIPTION OF DRAWINGS

FIGS. 1A–1C show genetic constructs of the invention.

DETAILED DESCRIPTION

The present invention provides new methods of detecting homologous recombination between introduced, heterologous nucleic acid molecules and endogenous plant DNA. The invention thus provides improved methods for modifying target plant nucleic acid sequence by transforming plant cells with nucleic acid sequences containing one or more sequences at least substantially identical with at least a portion of a target sequence.

In particular, the introduced molecules of the invention contain an internal recombinogenic substrate (IRS) which consists of a gene fusion between a fragment substantially identical to an endogenous target sequence cloned in-frame to a reporter sequence. The 5' regions of the gene fusion are deleted such that the DNA sequences responsible for expression of the fusion are absent, yielding an chimeric Δtarget gene::reporter gene fusion that will be effectively silent. The domains that are substantially identical to the target gene included in the IRS should be of sufficient length to allow homologous DNA recombination with either identical or very similar DNA sequences in vivo. Thus, the IRS typically consists of DNA from a target gene fused in frame to a reporter sequence and this construct lacks the necessary 5' transcription or translation signals to express the chimeric Δtarget gene::reporter gene translation product.

Either stably or transiently introduced copies of an IRS into plant cells will undergo a homologous recombination event between target-specific sequences present in the IRS with related sequences present in the genome. A homologous recombination event will restore the 5' target gene regulatory sequences to the gene fusion, yielding a recombinant gene chimera. Restoration of the endogenous 5' target gene regulatory sequences to the gene fusion will result in the transcription and translation of a chimeric fusion protein, which then imparts the reporter gene activity to the cell. The reporter gene activity (or properties inherent to the reporter gene) is then assayed to identify tissues showing expression of the reporter gene activity.

Use of homologous recombination in plants allows site-specific modification of particular target DNA sequences in an endogenous gene (e.g., exons, introns, and regulatory sequences). A number of targeted alterations are possible using the techniques of the present invention. For instance, the polypeptide expressed by the gene can be modified to alter properties of the expressed polypeptide. The modifications can include, for instance, substitutions, deletions, or insertions. In some embodiments recombinant alleles are produced that have sequences from both the endogenous target gene and the introduced sequence. These recombinant alleles preferably have activities not possessed by either gene from which they are derived. In other embodiments, the alterations can lead to elimination of all or substantially all of the activity of the expressed polypeptide. Alternatively, the modification can lead to inactivation of a gene by site-specific integration of a nucleotide sequence that disrupts expression.

If regulatory sequences are targeted, the timing and level of expression of a gene can be altered. In these embodiments the vectors of the invention contain a sufficient portion of the target promoter sequence to allow homologous recombination with the target sequence, but still prevent expression of the fusion sequence in the absence of homologous recombination. In this way, hybrid promoter sequences can be produced which have desired expression control properties. Thus, for instance, an endogenous promoter that is developmentally controlled can be modified to be constitutive or vice versa.

Preparation of Recombinant Vectors

To introduce the nucleic acid constructs of the invention, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence of interest fused to a reporter sequence, will be prepared according well known techniques and incorporated into an appropriate vector that lacks transcriptional and translational initiation regulatory sequences, such transcription of the fusion sequence will occur only in the event of homologous recombination.

Well known recombinant DNA methods are used to construct recombinant DNA molecules that comprise a targeting DNA containing sequences at least substantially identical to the target plant nucleotide sequence. Thus, the sequences used in the vectors of the invention will depend in large part on the target nucleotide sequence. The targeting DNA will typically be a variant of the target gene so that homologous recombination results in replacement of the target gene (or a portion of the gene) with the variant form. Incorporation of the targeting sequence by homologous recombination will result in expression of the reporter sequence, thereby allowing detection of the homologous recombination event.

The particular endogenous sequence targetted in the methods of the invention is not a critical aspect of the invention. Examples of genes that can be targetted using the present invention include genes conferring resistance to pathogens (for example, insects, fungi, bacteria and viruses), storage protein genes, herbicide resistance genes, and genes involved in biosynthetic pathways. Any part of the target gene can be modified. Thus, expression signal sequences (for example, promoter and terminator regions) and transcribed regions that encode a specific polypeptide can be targeted using the constructs of the invention.

The reporter sequence used in the invention is also not critical. The only requirement of the reporter sequence gene product is that it have some inherent activity or quality imparting a novel trait or phenotype that can be either monitored (non-selective or non-selectable screen) or directly selected for (i.e. novel activity that would impart resistance to a drug or other selective pressure for cell viability). When the activity of the recombinantly combined fusion gene product is desired, reporter sequence is typically selected to provide minimal inhibition of the activity of the fusion gene product. One of skill will recognize that, depending upon the activity of the fusion product, a number of means can be used to screen for fusion gene products having the desired function. Using these methods one of skill can make and test constructs to identify the minimal sequence required to provide a reporter activity and still provide a functional fusion gene product.

Non-selective reporter genes activities are generally preferred. Examples of non-selective reporter sequences include those whose gene product provides fluorescence, light emission, pigmentation, color, or change of morphology specific to the reporter gene activity. Suitable reporter genes are well known to those of skill in the art and include, for instance, β-glucuronidase (GUS), (Jefferson et al., *EMBO J.* 6:3901–3907 (1987)), firefly luciferase (LUC), (De Wet et al., *Mol. Cell. Biol.* 7:725–37 (1987)) or green fluorescent protein.

Selective reporter sequence activities include but are not limited to drug resistance, herbicide resistance, or resistance to either biotic or abiotic stress. For example, the marker may encode biocide resistance, particularly antibiotic resistance, such as resistance to kanamycin, G418, bleomycin, hygromycin, or herbicide resistance, such as resistance to chlorosulfuron or Basta.

Transformation

Recombinant vectors of the invention may be introduced into the genome of the desired plant host by a variety of conventional techniques. The present invention can be practiced with any explant for which transformation is possible. This includes, but is not limited to, leaf discs, stem explants, floral tissues, root tissue, embryogenic tissues, callus tissues, protoplasts, or suspension cells.

The vector may be introduced into the plant cell using techniques such as Agrobacterium-mediated transformation, electroporation, microinjection, or ballistic methods, such as DNA particle bombardment. Microinjection techniques are known in the art and well described in the scientific and patent literature. The introduction of DNA constructs using polyethylene glycol precipitation is described in Paszkowski et al. *EMBO J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

In most embodiments, the DNA constructs are combined with suitable T-DNA flanking regions and introduced into plant cells using a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as reporter gene activity. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The methods of the invention can be used to confer desired traits on essentially any plant. Thus, the invention has use over a broad range of plants, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea.

The means for selecting plants or plants cells in which homologous recombination has occurred will, of course, depend upon the particular reporter sequence used in the invention. For instance, detection of luciferase activity can be accomplished using video imaging equipment, as described in detail below.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

EXAMPLE

This example demonstrates use of an internal recombinogenic substrate (IRS) to identify and isolate rare germinal unequal cross-over events in *Arabidopsis thaliana* resulting in a gene duplication and the concomitant activation of a recombinant chimeric RUBISCO small subunit-luciferase reporter gene.

METHODS

Construction of IRS, Positive Control, and Plant Transformation:

Recombinant DNA constructs were made using standard procedures (see, e.g., Ausubel, F. M. (Greene Pub. Associates and Wiley-Interscience J. Wiley, New York) (1987)). JGJ188 consisted of a BamHI-PflMI-HindIII-BsmI-NarI linker generated by PCR amplification using pJGJ184 (promoterless Firefly Luciferase-nos 3' terminator subcloned in pBlueScript SK(+)) as a template and oligonucleotide primers o1 (5' TCCAGGAACCAGGGCGTATATCT 3'; SEQ ID NO:1)and o2 (5' CGGGATCCATTCACTG GAAGCTTCAGTGAATGCAAGCTGGAAGACG CCAAAAACATAAA 3'; SEQ ID NO:2) to generate a linker fragment that was then subcloned into pJGJ184 as a BamHI-NarI fragment. JGJ194 was a HindIII-BsmI RBCS1B genomic DNA fragment from pATS7 subcloned into pJGJ188 similarly cut. Deletion of the 5' RBCS1B regulatory sequences was accomplished by digesting pJGJ194 with PflMI and self-ligated to generate a ΔRBCS1B::LUC-NOS terminator gene fusion, pJGJ1196. pJGJ93 consisted of a ClaI-SalI RBCS2B–RBCS3B genomic DNA fragment reconstructed from a ClaI-SalI RBCS2B subclone from pATS17 and a SalI-SphI RBCS3B subclone from pATS5 both introduced into pJGJ86 (pBlueScript SK(+) with a modified polylinker to which a SphI site was added by PCR using oligonucleotide primers o4 (5' TTGAGCTCATAACT TCGTATAGCATACATTATACGAAGTTATCCACCGCG GTGGCGG 3'; SEQ ID NO:3) and o3 (5 ' AACTCGAGAA TAACTrCGTATAATGTATGCTATACGAAGTTATGCAT GCGTCGACG GTATCGATAAGC 3'; SEQ ID NO:4) and pBlueScript SK(+) as template). The IRS was generated by inserting the BamHI-ClaI fragment from pJGJ196 into pJGJ193 similarly cut, yielding pJGJ200. The IRS was subcloned into the T-DNA binary transformation vector pSLJ7292 (Jones, et al., *Transgenic Research*, 1:285–297 (1992)) as a SstI (partial)-XhoI fragment, yielding pJGJ203. pJGJ201 consisted of a 2.8 Kb BamHI-PflMI RBCS1B promoter containing fragment from pATS18 subcloned into pJGJI94 similarly cut; the intact RBCS1B promoter-RBCS1B::LUC fusion was subcloned from pJGJ201 into pSLJ7292 on a SstI-XhoI fragment, yielding pJGJ204. Transgenic plants were generated by mobilizing the recombinant binary transformation vectors by triparental mating with HB 101/pRK2013 into *Agrobacterium tumefaciens* strain GV3 101 which was used to perform vacuum infiltration transformation of *a. thaliana* Col-0 (Bechtold, et al., *Comptes Rendus de l'Academie des Sciences Serie III Sciences de la Vie*, 316:1194–1199 (1993)).

Imaging of Seedlings:

Seeds were grown on Vermiculite moistened with IX Hoaglands solution under continuous white light illumination. Twenty minutes before photon counting seedlings were sprayed with 0.5 mM synthetic D-Luciferin (BIOSYNTH AG, Switzerland) 0.01% Triton X-100 solution. An intensified CCD video camera (Hamamatsu Photonics, model C2400 47) in conjunction with a Image Intensifier Controller (Hamamatsu Photonics, model M4314) and Image Processor (Hamamatsu Photonics, Argus 50) was used to image seedlings within a Hamamatsu Photonics imaging chamber, model A417, mounted with a Xenon CM 120 lens (Schneider, Bad Kreuznach, Germany). Each tray was imaged for 10 minutes in photon counting mode; if a suspected luc$^+$ signal appeared, the tray was imaged for an additional 10 minutes. Argus 50 software was used to collect and process digital images; photon counting imaging was performed in slice/gravity mode while reflected geen light imaging was performed using integration mode.

PCR of Genomic DNA:

Genomic DNA was isolated using a CTAB miniprep protocol. Approximately, 100 ng of genomic DNA was used in each PCR reaction. Amplification consisted of one cycle of 94° C.; 35 cycles of 1 min 94° C., 1 min at annealing temperature appropriate to each oligonucleotide pair, min/ Kb of expected size fragment at 72° C.; followed by 7 min 72° C. extension. Various oligonucleotide pairs and respective annealing temperatures utilized were as follows: o13 (5' CAAAAGAAAGATAAGGGTGTCAA 3'; SEQ ID NO:5) and o14 (5' CCTTTCTTTATGTTTTTGGCGTCTTC 3'; SEQ ID NO:6), 53° C.; o26 (5' CTAATTTAATTTTGGGC-GACTGA 3'; SEQ ID NO:7) and o29 5' CAACAGA-CAATCGGCTGCTC 3'; SEQ ID NO:8), 55° C.; o37 (5' CCTTGTGATCCTTTTCCCTAC 3'; SEQ ID NO:9) and o22 (5' TCTTTATGTTTTTGGCGTCTT 3'; SEQ ID NO:10), 52° C.

RESULTS AND DISCUSSION

Figure 1:
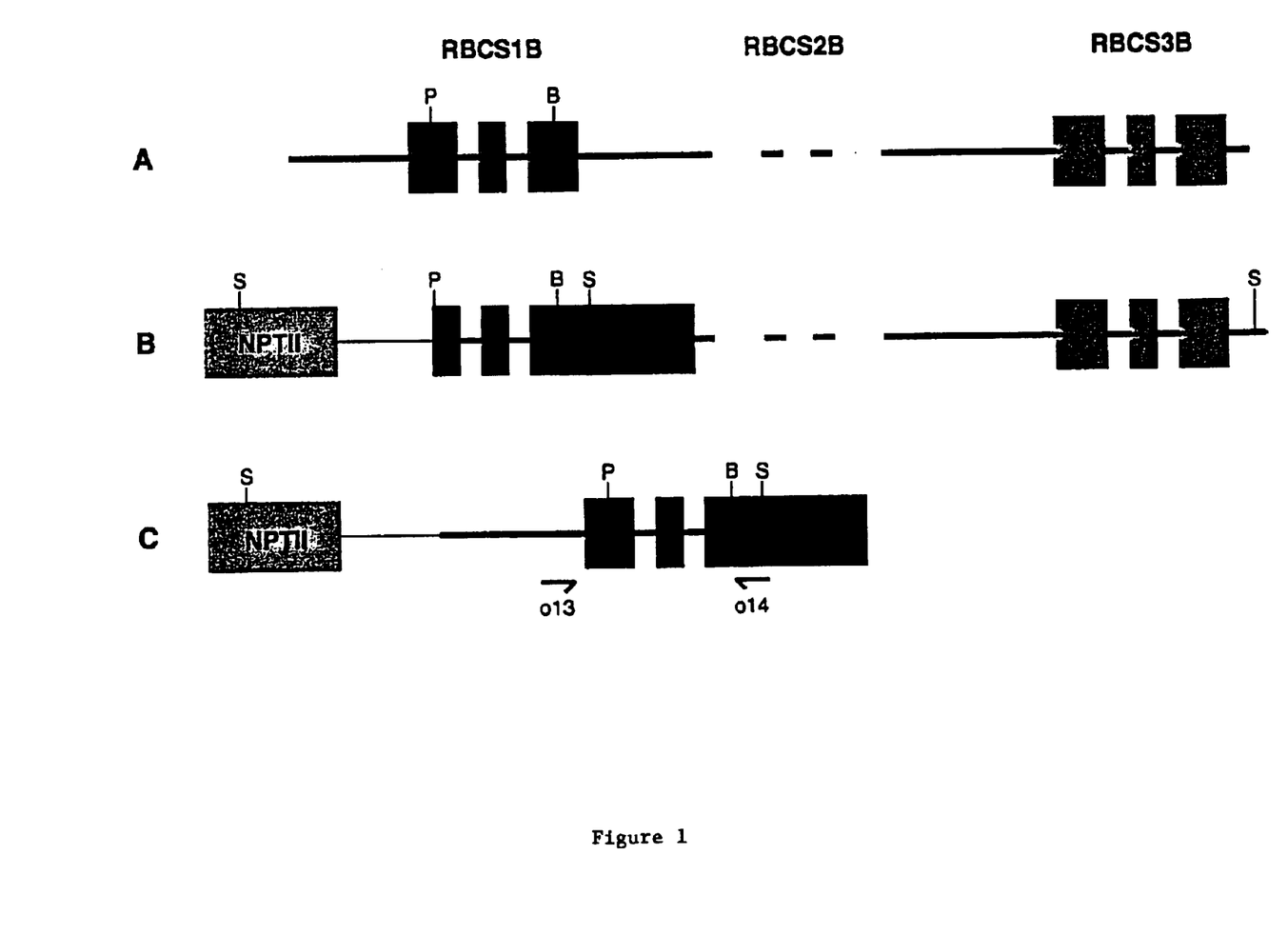
FIG. 1A shows the *Arabidopsis thaliana* RBCSB locus with black line indicating noncoding genomic DNA. Exons are shown in blocks (RBCS1B, RBCS2B, and RBCS3B, respectively). Exon size is not to scale but rather represents genic organization.
FIG. 1B shows an IRS construct used to make transgenic plants: NPTII gene shown in gray; ΔRBCS1B::LUC fusion consisted of RBCS1B sequences spanning from the PflMI site in RBCS1B exon I to the BsmI site in exon III; Firefly Luciferase nos 3' terminator is cloned in frame to the truncated RBCS1B exon III. RBCS2B RBCS3B sequences normally downstream of RBCS1B were placed 3' to the ΔRBCS1B::LUC fusion.
FIG. 1C shows a positive control construct (pJGJ204) consisting of a RBCS1B promoter RBCS1B::LUC gene fusion. Half arrows represent the approximate location and direction of oligonucleotide primers (o13 and o14) used in PCR reactions. Restriction enzymes: P, PflMI; B, BsmI; and S, Sphl.

In *Arabidopsis thaliana*, three of the four genes encoding the small subunit of RUBISCO are present in a tandem array constituting the RBCSB locus (Krebbers, et al., *Plant Mol. Biol.*, 11:745–760 (1988)) (FIG. 1A). This gene configuration and high degree of sequence identity between the paralogous RBCSB genes, it was predicted that the RBCSB locus would be susceptible to unequal cross-over events leading to both gene duplication and recombinant RBCSB genes. In order to directly identify and isolate the products of cross-over, an IRS was constructed such that the conditional expression of a Firefly luciferase gene was dependent on a cross-over event between the paralogous RBCSB genes. Important attributes of the IRS are shown in FIG. 1B.

A ΔRBCS1B::LUC reporter gene fusion consisted of replacing part of RBCS1B exon III with an in-frame gene fusion to the Firefly Luciferase gene (LUC); furthermore, sequences 5' to the PflMI site in RBCS1B were also deleted. Since the ΔRBCS1B::LUC reporter gene fusion lacked the 5' RBCS1B sequences normally required for transcription and translation it did not express luciferase activity (luc$^-$). 3' to ΔRBCS1B::LUC, genomic DNA normally present downstream of RBCS1B (RBCS2B–RBCS3B) was positioned such that near-normal spacing between the three genes was maintained (FIG. 1B). Several stably transformed IRS transgenic lines were generated in an *A. thaliana* ecotype Col0 backgound. A homozygous derivative of AtJGJ203.10, containing a single random IRS insertion, was crossed with a control line, AtJGJ7292.9, generating a F1 population of approximately 10,000 plants hemizygous for each transgenic locus. This F1 population was allowed to self-fertilize, yielding a F2 population with more than 2 million seed.

Three types of DNA recombination events could lead to F2 plants with phenotypic luciferase activity (luc$^+$): i, an illegitimate DNA recombination event bringing an unrelated transcription unit upstream of the ΔRBCS1B::LUC gene; ii, an intermolecular homologous recombination event between an endogenous RBCSB gene on Chromosome V; or iii, an intermolecular unequal sister chromatid homologous recombination event between adjacent RBCSB sequences present in the IRS. In order to detect the above recombination events, extremely sensitive single photon counting and imaging video equipment (Furuya, et al., *Instrumentation in photomorphogenesis research*., 1-29-40 (Kluwer Academic Publishing, Dordrecht, Boston, London) (1994)) was used to image large numbers of F2 seedlings sprayed with a dilute solution of luciferin, the substrate for Firefly luciferase. To do this, trays containing over 7,500 5 day old seedlings were sprayed with Luciferin and imaged in slice/gravity photon counting mode; the majority of trays did not show any photon emission above background levels level of detection. However, occasional trays demonstrated a distinct photon emission point source. While the intensified video imaging camera can image reflected green light in integration mode, the image quality is poor and it is impossible to identify individual luc+ seedlings. However, by marking the approximate location of the photon emission source on the video monitor during photon counting imaging, one can then subsequently approximate the same location on the tray during reflected green light imaging by placing tooth picks on the tray in real time. The accuracy of this estimation can confirmed by using the ARGUS-50 software to superimpose the photon counting image upon the reflected light image. Then approximately 40 individual seedlings were removed from the region of photon emission and transferred to a water agar plate making sure to separate individual seedlings. Photon counting imaging and reflected green light imaging were repeated to generate a superimposed image, allowing the unambiguous identification the luc+ seedling. Luc+ plants were consistently observed at an average frequency of 2.5×10$^{-6}$. Since only ten minutes of photon-counting was sufficient for initial detection of a luc$^+$ seedling, this assay allowed the rapid screening of very large populations of seedlings (>1.1 million seedlings in 25 hours of camera imaging time). Three luc$^+$ seedlings, derived from two independent crosses, were isolated from a population of >1.1 million observed F2 seedlings.

In order to determine if an homologous recombination event had positioned a RBCSB promoter upstream of the previously silent ΔRBCS1B::LUC reporter gene, genomic DNA from various lines were subjected to PCR analysis using a LUC-specific oligonucleotide primer in conjunction with a primer that binds to a 14 bp conserved sequence present in all Arabidopsis RBCS promoters (FIG. 1C, o14 and o13, respectively). Genomic DNA from all luc$^+$ lines yielded a ≈0.9 Kb PCR fragment, whereas genomic DNA from luc lines did not yield an equivalent size fragment. This indicated that the luc$^+$ phenotype resulted from the fusion of a RBCSB promoter to the LUC reporter gene, suggesting this fusion was the result of homologous recombination, rather than an illegitimate recombination event, for instance a promoter/enhancer trap-effect (Sundaresan, et al., *Genes & Development*, 9:1797–1810 (1995)).

Figure 2:
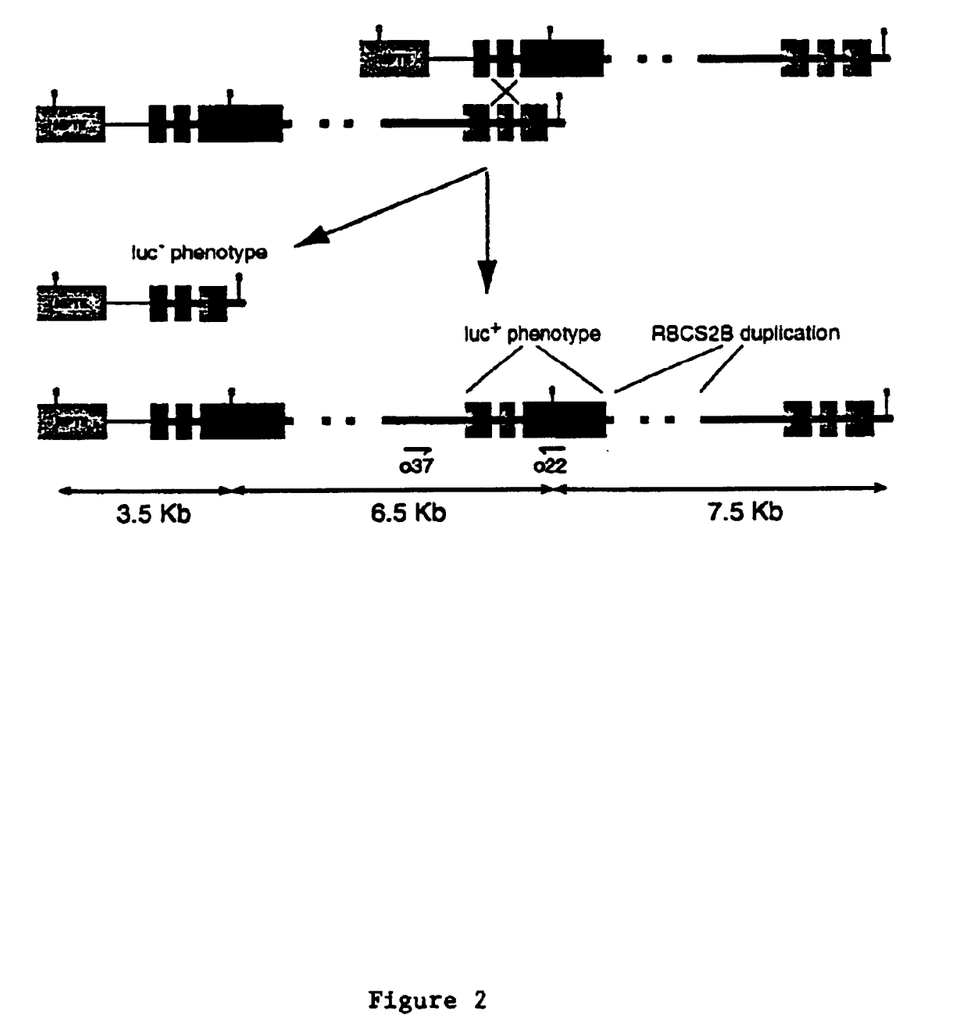
FIG. 2 shows unequal interchromosomal crossing over of misaligned sister chromatids such that the RBCS3B gene on one sister chromatid underwent reciprocal recombination with the ΔRBCS1B::LUC gene on the other sister chromatid. This cross-over resulted in two recombinant chromatids. One recombinant chromatid contained a single recombinant RBCS1B/3B gene. The reciprocal recombinant chromatid contained an intact IRS gene complement and two gene duplications: a recombinant RBCS3B/1B::LUC chimeric gene (imparting a luc$^+$ phenotype) and an adjacent RBCS2B gene. Panel C, genomic DNA was subject to PCR analysis with one oligonucleotide primer specific to a RBCS2B-3B intergenic region (o37) and one primer specific to LUC (o22).

In order to determine which RBCS promoter was responsible for the activation of the LUC reporter gene, SphI digested genomic DNA, from luc$^+$ and luc$^-$ seedlings, was subjected to Southern blot analysis using a $^{32}$PCTP labeled LUC probe. Two LUC hybridizing bands (3.5 Kb and 7.5 Kb) were observed in independent IRS parental lines and the three luc$^+$ isolates. If a homologous recombination event occurred between the randomly integrated IRS and the endogenous RBCSB locus on Chromosome 5 it would generate one additional LUC hybridizing band (either 4.5 Kb, 7.5 Kb, or 11.5 Kb) depending upon which RBCSB gene crossed-over (RBCS1B, RBCS2B, or RBCS3B, respectively); however, a band of these expected sizes was not observed. Instead, a novel 6.5 Kb LUC hybridizing fragment was only observed in genomic DNA from the luc$^+$ F2 isolates. The 6.5 Kb SphI fragment is consistent with a homologous recombination event between two misaligned sister chromatids, such that the ΔRBCS1B::LUC gene on one sister chromatid crossed over with the RBCS3B gene present in the IRS on the other sister chromatid (FIG. 2). Such a homologous recombination event would generate a RBCS2B duplication and an additional recombinant chimeric RBCS3B/1B::LUC gene, imparting a luc$^+$ phenotype. To test the assertion that RBCS3B promoter sequences were responsible for expression of the LUC gene, genomic DNA was subjected to PCR analysis using a primer specific to a unique RBCS2B–3B intergenic region in conjunction with a LUC specific primer (FIG. 2, o37 and o22, respectively). As expected, luc$^+$ lines containing the 6.5 Kb LUC hybridizing SphI fragment yielded the expected 2.8 Kb PCR fragment, whereas luc lines lacking the 6.5 Kb SphI fragment did not amplify the expected fragment. This confirmed that RBCS3B promoter sequences were positioned upstream of the LUC gene.

In the postulated recombinant RBCS3B/1B::LUC chimera, the DNA sequences upstream of the PflMI site present in the original ΔRBCS1B::LUC fusion should be replaced with RBCS3B specific promoter, 5' untranslated leader, and exon I sequences. The RBCS3B gene has a 21 bp insertion within the 5' untranslated leader not present in the other RBCSB genes: consequently, a recombinant chimeric RBCS3B/1B::LUC gene should amplify a proportionally larger PCR fragment with primers o13 and o14 relative to an intact RBCS1B promoter-RBCS1B::LUC fusion. Consistent with this assertion, the F2 luc$^+$ isolates yielded a slightly larger PCR fragment. The 6GI and AtJGJ204.7 PCR fragments amplified with o13 and o14 were subcloned, sequenced, and aligned to the genomic RBCS1B and RBCS3B sequences. DNA sequencing from the 5' end indicated that all nucleotides unique to the RBCS3B promoter, 5' untranslated leader, and exon I were present in the luc$^+$ line 6GI. Moreover, RBCS3B signatures continued 3' to the RBCS1B PflMI site, indicating that the cross-over event leading to the recombinant RBCS3B/1B::LUC chimera occurred within the short region of shared DNA sequence similarity between ΔRBCS1B::LUC and RBCS3B located on the IRS. These data provided definitive evidence that a recombinant RBCS3B/1B::LUC chimera was responsible for the luc$^+$ phenotype. Furthermore, lines 4A1, 6F1, 6G1 showed a 3:1 segregation ratio of the luc$^-$ trait in the F3 population, indicating the recombinant RBCS3B/1B::LUC chimera was present as hemizygous gene in the original F2 luc$^+$ isolates.

The reproducibility of these unequal cross-over events was demonstrated in unrelated experiments in which two independent IRS lines were crossed to unspecified transgenic lines, consistently yielding F2 populations with 3–5 luc+ seedlings per 1.1 million observed plants; likewise, in all cases, the luc+ phenotype was due to a recombinant RBCS3B/1B::LUC chimeric gene, data not shown. Given the low and reproducible frequency of the RBCS3B/1B::LUC recombinants, they likely represent an accurate measurement of the frequency of meiotic unequal crossing over between sister chromatids in Arabidopsis thaliana ($3 \times 10^{-6}$). It is noteworthy that this frequency falls within the range of the spontaneous mutation rate ($10^{-6}$) suggesting that the contribution of meiotic unequal cross-over events to genome evolution may be as significant as spontaneous mutation. The observed frequency of unequal cross-over was consistent with a previous report (Assad et al., *Genetics*, 132:553–566 (1992)) of plant meiotic cross-over events between direct repeats of non-allelic mutant drug resistance genes leading to restoration of a functional gene. However, in contrast to Assad et al., we did not observe gene conversion events, nor did we observe homologous recombination between the IRS and the endogenous RBCSB locus. While the ΔRBCS1B and RBCS2B genes shared sufficient sequence similarity for homologous recombination, no recombinant RBCS2B/1B::LUC chimeric luc+ plants were isolated. The simplest explanation for this was due to the fact that most of the RBCS2B promoter was deleted in the construction of the IRS, so a recombinant RBCS2B/1B::LUC chimera would be phenotypically silent and thus go undetected in this screen.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of identifying homologous recombination in plant cells, the method comprising:

contacting a plurality of plant cells with a heterologous nucleic acid molecule comprising a fusion polynucleotide comprising a nucleotide sequence encoding a polypeptide sequence of interest linked to a reporter sequence, wherein the nucleotide sequence encoding the polypeptide sequence of interest targets an endogenous gene and wherein the nucleic acid molecule lacks sequences necessary for expression of the fusion polynucleotide gene product in a cell; and detecting the presence of the reporter activity in the plant cells, thereby identifying plant cells in which homologous recombination has occurred between the introduced heterologous nucleic acid molecule and endogenous plant DNA.

2. The method of claim 1, wherein the step of contacting is carried out using a T-DNA vector.

3. The method of claim 1, further comprising the step of regenerating plants from the plant cells before the step of detecting the presence of the fusion sequence gene product.

4. The method of claim 1, wherein the reporter sequence is non-selective.

5. The method of claim 4, wherein the non-selective reporter sequence encodes luciferase.

6. The method of claim 5, wherein the step of detecting is carried out using video imaging equipment.

7. The method of claim 1, wherein the plant cell is Arabidopsis.

8. The method of claim 1, further comprising introducing a selectable marker into the plant cells and performing a selection step to identify plants having the selectable marker.

9. The method of claim 8, wherein the selectable marker is encoded by a nucleic acid sequence comprised by the heterologous nucleic acid molecule.

* * * * *

UNITED STATES PATENT AND TRADEMARK OFFICE
CERTIFICATE OF CORRECTION

PATENT NO. : 6,781,032 B1 Page 1 of 1
DATED : August 24, 2004
INVENTOR(S) : Wilhelm Gruissem It is certified that error appears in the above-identified patent and that said Letters Patent is hereby corrected as shown below:

<u>Title page,</u>
Item [73], Assignee, add -- Hitachi, Ltd.
                        Hatoyoma, Saitama, Japan --.

Signed and Sealed this

Thirtieth Day of May, 2006

JON W. DUDAS
*Director of the United States Patent and Trademark Office*

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: oligonucleotide primer o1

<400> SEQUENCE: 1
tccaggaacc agggcgtata tct                     23

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: oligonucleotide primer o2

<400> SEQUENCE: 2
cgggatccat tcactggaag cttcagtgaa tgcaagctgg aagacgccaa aaacataaa     59

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: oligonucleotide primer o4

<400> SEQUENCE: 3
ttgagctcat aacttcgtat agcatacatt atacgaagtt atccaccgcg gtggcgg       57

<210> SEQ ID NO 4
<211> LENGTH: 68
<212> TYPE: DNA
<213> ORGANISM: Artificial Sequence
<220> FEATURE:
<223> OTHER INFORMATION: Description of Artificial Sequence: oligonucleotide primer o3

<400> SEQUENCE: 4
aactcgagaa taacttcgta taatgtatgc tatacgaagt tatgcatgcg tcgacggtat    60
cgataagc                                                            68

-continued

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:
      oligonucleotide o13

<400> SEQUENCE: 5
caaaagaaag ataagggtgt caa                                              23

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      oligonucleotide o14

<400> SEQUENCE: 6
cctttcttta tgtttttggc gtcttc                                           26

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:
      oligonucleotide o26

<400> SEQUENCE: 7
ctaatttaat tttgggcgac tga                                              23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      oligonucleotide o29

<400> SEQUENCE: 8
caacagacaa tcggctgctc                                                  20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
      oligonucleotide o37

<400> SEQUENCE: 9
ccttgtgatc cttttcccta c                                                21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:
      oligonucleotide o22

<400> SEQUENCE: 10
tctttatgtt tttggcgtct t                                                21